(12) United States Patent
Horikoshi et al.

(10) Patent No.: US 11,540,839 B2
(45) Date of Patent: Jan. 3, 2023

(54) CLIP UNIT, MUCOUS MEMBRANE LIFTING SYSTEM, AND MUCOUS MEMBRANE LIFTING METHOD

(71) Applicant: OLYMPUS CORPORATION, Hachioji (JP)

(72) Inventors: Risako Horikoshi, Tokyo (JP); Nobuko Matsuo, Tokyo (JP); Masatoshi Tonomura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/022,168

(22) Filed: Sep. 16, 2020

(65) Prior Publication Data

US 2021/0000475 A1   Jan. 7, 2021

Related U.S. Application Data

(63) Continuation of application No. PCT/JP2018/030945, filed on Aug. 22, 2018.

(51) Int. Cl.
*A61B 17/122* (2006.01)
*A61B 17/29* (2006.01)
(Continued)

(52) U.S. Cl.
CPC ............ *A61B 17/122* (2013.01); *A61B 17/29* (2013.01); *A61B 17/1285* (2013.01); *A61B 2017/00296* (2013.01); *A61B 2017/00818* (2013.01); *A61B 2017/00867* (2013.01); *A61B 2217/005* (2013.01)

(58) Field of Classification Search
CPC ... A61B 17/122; A61B 17/29; A61B 17/1285; A61B 2017/00296; A61B 2017/00818; A61B 2017/00867; A61B 2217/005
See application file for complete search history.

(56) References Cited

U.S. PATENT DOCUMENTS 5,474,572 A    12/1995  Hayhurst
5,569,274 A *  10/1996  Rapacki ............ A61B 18/1442
                                                    606/151
(Continued)

FOREIGN PATENT DOCUMENTS

JP    H11-513292 A    11/1999
JP    2004-016662 A    1/2004
(Continued)

OTHER PUBLICATIONS

Sep. 25, 2018 International Search Report issued in International Patent Application No. PCT/JP2018/030945.

*Primary Examiner* — Brooke Labranche
(74) *Attorney, Agent, or Firm* — Oliff PLC

(57) ABSTRACT

A clip unit includes: an arm portion including arms extending from a proximal end portion to a distal end portion so as to be openable and closeable; a holder than can hold the arms in a closed state by accommodating the proximal end portion of the arm portion; and a thread grip attached to at least one of the arms and positioned between the arms. In a state where the arms are spread open, a dimension of the thread grip in the opening/closing direction of the arms is equal to or larger than a distance between the arms in the closed state. The thread can be elastically deformed in the closed state.

7 Claims, 9 Drawing Sheets

(51) Int. Cl.
  *A61B 17/128* (2006.01)
  *A61B 17/00* (2006.01)

(56) References Cited

U.S. PATENT DOCUMENTS

| | | | |
|---|---|---|---|
| 2002/0111534 A1* | 8/2002 | Suzuki | A61B 17/0469 600/102 |
| 2010/0152753 A1* | 6/2010 | Menn | A61B 17/00234 606/158 |
| 2014/0018829 A1 | 1/2014 | Patani | |

FOREIGN PATENT DOCUMENTS

| JP | 2005-103107 A | 4/2005 |
|---|---|---|
| WO | 97/13466 A1 | 4/1997 |

* cited by examiner

CLIP UNIT, MUCOUS MEMBRANE LIFTING SYSTEM, AND MUCOUS MEMBRANE LIFTING METHOD

CROSS REFERENCE TO RELATED APPLICATIONS

This application is a continuation application based on a PCT Patent Application No. PCT/JP2018/030945, filed on Aug. 22, 2018, the entire content of which is hereby incorporated by reference.

BACKGROUND

Technical Field

The present disclosure relates to a clip unit, a mucous membrane lifting system, and a mucous membrane lifting method.

Background

The treatment of endoscopically removing lesions of the gastrointestinal tract is widely used as a radical treatment capable of collectively excising lesions while being minimally invasive.

In endoscopic submucosal dissection (ESD), the mucous membrane layer around the region containing the lesion is incised and then the submucous membrane layer is detached to excise the lesion.

In the submucous membrane layer peeling work, there is a need that the submucous membrane layer, which constitutes the innermost layer of the digestive tract, is appropriately pulled up to ensure that the submucous membrane layer is captured in the field of view of the endoscope, and also proceed while applying appropriate traction to the peeled site.

However, the inside of the digestive tract is an extremely limited space, and it is difficult to apply appropriate traction to the ablation site depending on the position of the lesion and the posture of the patient. For this reason, the peeling operation of the submucous membrane layer is difficult and time-consuming.

There is a mucous membrane traction tool that stretches an elastic portion and pulls a mucous membrane layer that is to be incised and peeled.

However, in the mucous membrane traction tool, the amount of traction force is defined by the restoring force of the elastic portion, and thus it is difficult to adjust the traction. In addition, since a first clamping member is attached to the mucous membrane to be incised and peeled off and a second clamping member is attached to another mucous membrane, it is difficult to make the distance between the mucous membrane to be incised and peeled off and the other mucous membrane be shorter than the length of the mucous membrane retractor extending therebetween.

From the above, it is difficult for such a mucous membrane traction tool to change the amount of traction and the size of traction during the separation.

SUMMARY

The present disclosure provides a clip unit, a mucous membrane lifting system, and a mucous membrane lifting method that can easily change the amount of traction of the mucous membrane even during mucous membrane peeling.

According to an aspect of the present disclosure, a clip unit for lifting a mucous membrane includes an arm portion including a first arm and a second arm extending from a proximal end portion to respective distal end portions so as to be openable and closeable with respect to each other. The first arm and the second arm can each include a claw at a distal end thereof. The claw of the first arm and the claw of the second arm can sandwich a biological tissue. The clip unit also includes a holder that can hold the first arm and the second arm in a closed state by accommodating a proximal end portion of the arm portion; and a thread grip attached to at least one of the first arm and the second arm at a position on a proximal end side of the claw. The thread grip is located between the first arm and the second arm, and in a state where the first arm and the second arm are spread open, a dimension of the thread grip in the opening/closing direction of the first arm and the second arm is equal to or larger than a distance between the first arm and the second arm in the closed state. The thread grip can be elastically deformed when the first arm and the second arm are in the closed state.

A hardness of a surface of the thread grip that can comes into contact with the thread may be lower than a hardness of a surface of the first arm and the second arm.

The clip unit may further include: a thread to be sandwiched by the thread grip. The thread grip may include a first member attached to the first arm, and a second member attached to the second arm. A diameter of the thread may be smaller than a distance between the first member and the second member in a state where the first arm and the second arm are spread open, and may be larger than a distance between the first member and the second member in the closed state.

In one aspect, the first member may be rotatably attached to the first arm. A cross section of at least a part of the first member and the second member may have a convex shape. The convex shape may extend in a direction inclined with respect to a first line extending between the first arm and the second arm, and a second line orthogonal to the first line in the cross section. The first arm and the first member may be positioned so that an apex of the convex shape of the first member and an apex of the convex shape of the second member are close to each other due to a frictional force generated between the first arm and the first member. A sum of a distance between the first arm and the apex of the convex shape of the first member in the cross section and a distance between the second arm and the apex of the convex shape of the second member in the cross section may be longer than a distance between the first arm and the second arm in the closed state.

In another aspect, a cross section of at least a part of the first member and the second member may have a plurality of convex portions extending in directions approaching each other. In the cross section, each of the plurality of convex portions may have an inclined surface that is inclined with respect to a first line connecting the first arm and the second arm and a second line orthogonal to the first line.

The clip unit may further include: an operation wire that has a distal end and a proximal end and is provided so as to be movable along a longitudinal axis; a connector which is located between and connects the proximal end portion of the arm portion and the operation wire; and an operation unit connected to the proximal end portion of the operation wire, configured to be capable of pulling the operation wire until a connection between the proximal end and the operation wire can be released.

According to an aspect of the present disclosure, a mucous membrane lifting system includes: a clip unit such as that discussed above; a thread including a first end portion designed to be fixed to the mucous membrane, a second end portion different from the first end portion, and an intermediate portion provided between the first end portion and the second end portion and sandwiched by the thread grip of the clip unit; and grasping forceps configured to grip the second end portion of the thread to pull the thread.

According to an aspect of the present disclosure, a mucous membrane lifting method includes: a step A of incising at least a part of a mucous membrane around a region containing a lesion, in the digestive tract; a step B of fixing a first end of a thread to the mucous membrane in the region containing the lesion; a step C of passing an intermediate portion of the thread between a first arm and a second arm of a clip unit, a step D of sandwiching a tube wall at a position facing the region including the lesion between the first arm and the second arm, with the thread between the first arm and the second arm, after the step C; and a step E of pulling a second end of the thread to move the thread with respect to the clip unit to lift the mucous membrane in the region including the lesion, after the step D, wherein, the thread is supported by a frictional force generated between the first arm and the second arm and the thread such that a lifted state of the mucous membrane is maintained.

The clip unit used in the method may include any of the additional features disclosed herein, including, for example, a thread grip attached to the first arm and the second arm. In the step D, the thread may be sandwiched by the thread grip.

In the step D, the first arm and the second arm may be in a closed state, and the thread grip may be elastically deformed between the first arm and the second arm.

The thread grip may include a first member attached to the first arm, and a second member attached to the second arm. In one aspect, the first member may be rotatably attached to the first arm. A cross section of at least a part of the first member and the second member may have a convex shape. The convex shape may extend in a direction inclined with respect to a first line extending between the first arm and the second arm and a second line orthogonal to the first line in the cross section. The first arm and the first member may be positioned so that an apex of the convex shape of the first member and an apex of the convex shape of the second member are close to each other due to a frictional force generated between the first arm and the first member. A sum of a distance between the first arm and the apex of the convex shape of the first member in the cross section and a distance between the second arm and the apex of the convex shape of the second member in the cross section may be longer than a distance between the first arm and the second arm in the closed state. In the step C, the thread may be sandwiched between the convex shape of the first member and the convex shape of the second member.

In another aspect, a cross section of at least a part of the first member and the second member may have a plurality of convex portions extending in directions approaching each other. Each of the plurality of convex portions may include an inclined surface that is inclined with respect to a first line connecting the first arm and the second arm and a second line orthogonal to the first line, in the cross section. In the step C, the thread may be sandwiched between the convex portion of the first member and the convex portion of the second member.

In the step C, a second end of the thread may be passed from the first line toward the apex of the convex portion of the first member.

In the step C, the second end of the thread may be passed in a direction in which the inclined surface extends toward the apex of the convex portion in each of the plurality of convex portions.

According to the present disclosure, the amount of traction of the mucous membrane and the size of the traction can be easily changed even during the mucous membrane peeling.

DETAILED DESCRIPTION

An exemplary embodiment of the present disclosure will be described with reference to FIGS. 1 to 10.

Figure 1:
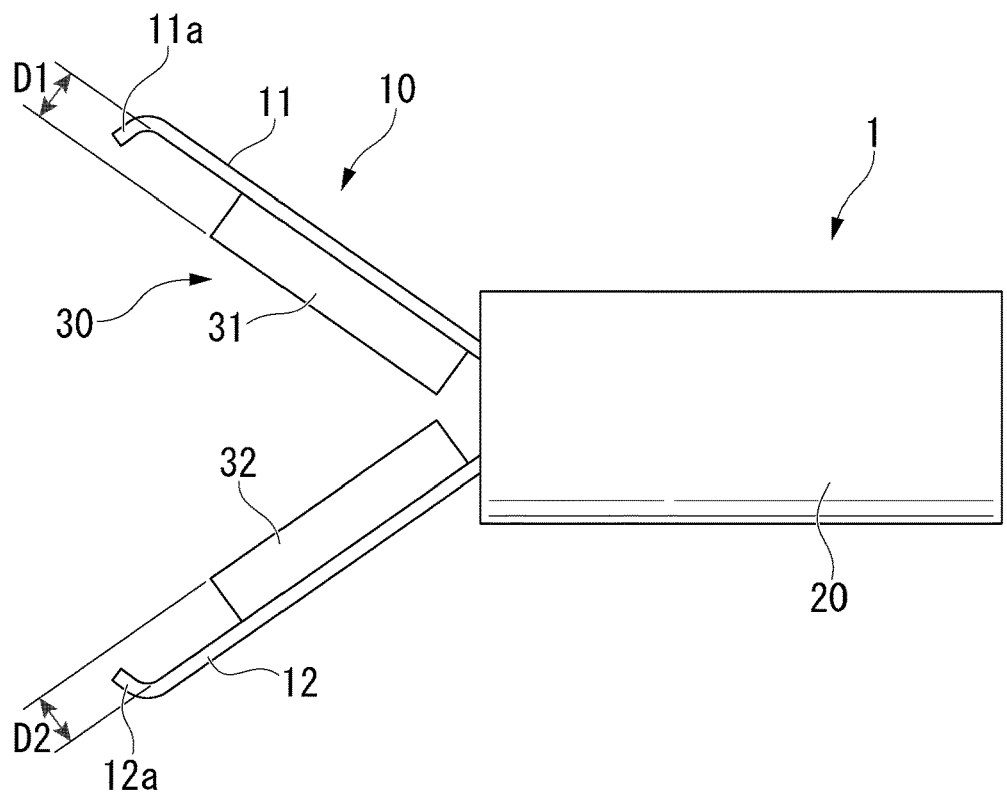
FIG. 1 is an external view of a clip unit according to an exemplary embodiment of the present disclosure.
Figure 2:
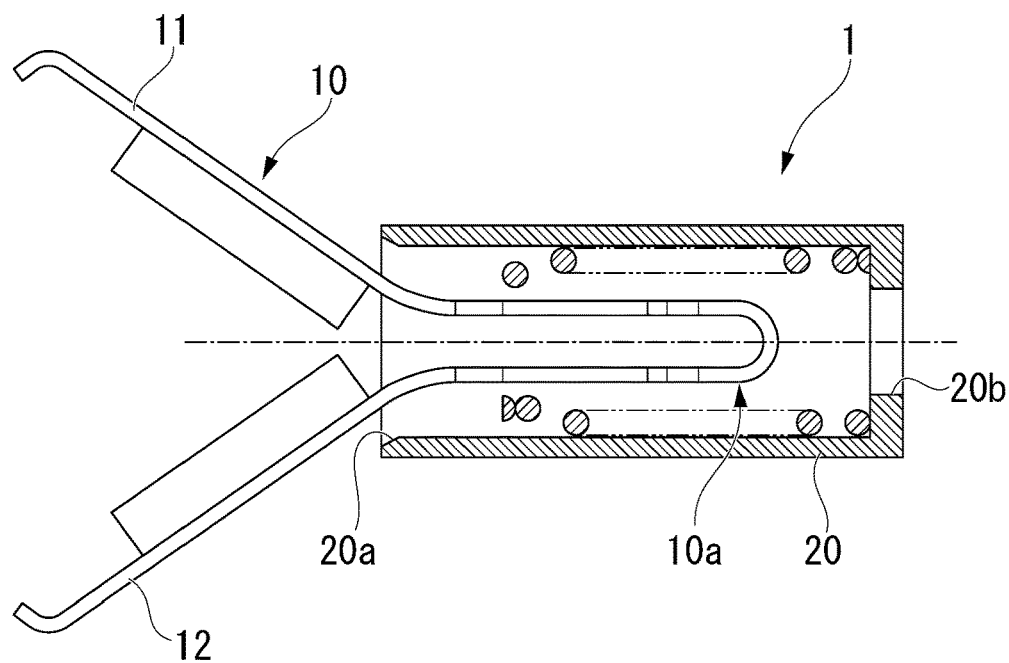
FIG. 2 is a sectional view of the clip unit.

FIG. 1 is a view showing the outer appearance of the clip unit 1 of this embodiment. FIG. 2 is a cross-sectional view of the clip unit 1. As shown in FIG. 1, the clip unit 1 includes an arm portion 10, a pressing tube (holder) 20 in which a part of the arm portion 10 is accommodated, and a thread gripping portion (thread grip) 30 attached to the arm portion 10.

The arm unit 10 has a pair of arms, a first arm 11 and a second arm 12. The first arm 11 and the second arm 12 have claws 11a and 12a at their distal ends. As shown in FIG. 2, at the proximal end portion 10a of the arm portion 10, the first arm portion 11 and the second arm 12 are connected.

The arm portion 10 is formed of a metal including an alloy. Examples of the material of the arm portion 10 include stainless steel, cobalt chrome alloy, nickel titanium alloy and the like.

The first arm 11 and the second arm 12 are in the spread opened state in the initial state shown in FIG. 1. When the first arm 11 and the second arm 12 approach each other from the initial state, an elastic force of the material causes a biasing force to return to the initial state.

The pressing tube 20 is a tubular member made of metal, resin, or the like. The proximal end portion of the arm portion 10 is housed in the pressing tube 20. The distal end portion of the arm portion 10 protrudes from the distal end opening 20a of the pressing tube. The proximal end opening 20b of the pressing tube 20 is smaller than the distal end opening 20a.

Figure 3:
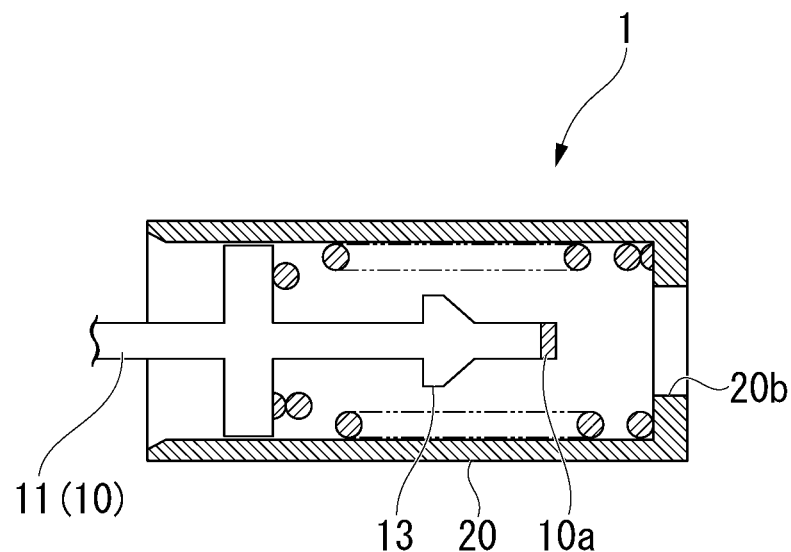
FIG. 3 is a partial cross-sectional view of the clip unit seen from a direction different from that of FIG. 2.

FIG. 3 is a view of the inside of the presser pipe 20 viewed from a direction different from that in FIG. 2. As shown in FIG. 3, a locking portion 13 is provided at an intermediate portion of each arm of the arm portion 10, and in the locking portion 13, the dimensions of the arms 11 and 12 in the width direction are large (Only the first arm 11 is visible in FIG. 3). Each locking portion 13 can pass through the proximal end opening 20b when the first arm 11 and the second arm 12 approach each other. When the first arm 11 and the second arm 12 are separated after passing through the proximal end opening 20b, the locking portion 13 cannot pass through the proximal end opening 20b.

The basic structures of the arm portion 10 and the presser pipe 20 described above are known and are disclosed in, for example, PCT International Publication No. WO 2014/181676.

The thread gripping portion 30 has a first member 31 attached to the first arm 11 and a second member 32 attached to the second arm 12. As a method of attaching the first member 31 and the second member 32 to the arm, adhesion or the like can be exemplified.

The first member 31 and the second member 32 are formed of a material that elastically deforms. That is, the Young's modulus of the first member 31 and the second member 32 is smaller than the Young's modulus of the arm portion 10. Examples of the material of the first member 31 and the second member 32 include rubber, silicone, elastomer and the like. The sum of the dimension D1 of the first member 31 (see FIG. 1) and the dimension D2 of the second member 32 in the direction in which the first arm 11 and the second arm 12 approach and separate (opening/closing direction of the arm portion 10) is not less than the distance between the first arm 11 and the second arm 12 when the arm portion 10 is closed. That is, in a state where the arm portion 10 is closed, the first member 31 and the second member 32 are elastically deformed.

In a state where the sum of the dimension D1 and the dimension D2 is excessively large, depending on the hardness of the first member 31 and the second member 32, the tissue may be hindered from being sandwiched by the claws 11a and 12a, or the tissue sandwiching force may be excessively reduced. From this viewpoint, the sum of the dimension D1 and the dimension D2 may be a range from a value slightly smaller than the distance between the first arm 11 and the second arm 12 in a state where the arm part 10 is closed (for example, a value equal to or smaller than the diameter of the thread to be clamped) to a value slightly larger than that value.

The first member 31 and the second member 32 are softer than the first arm 11 and the second arm 12. That is, the Vickers hardness of the surfaces of the first member 31 and the second member 32 is lower than the Vickers hardness of the surfaces of the first arm 11 and the second arm 12.

The operation when using the clip unit 1 having the above-described configuration will be described. Since the clip unit 1 can be suitably used when lifting a mucous membrane during a procedure such as ESD, the flow of a mucous membrane lifting method using the clip unit 1 will be described below.

First, a physician or assistant inserts the endoscope into the digestive tract and advances the distal end of the endoscope to the vicinity of the lesion to be treated. The physician observes the lesion endoscopically, examines the size of the margin around the lesion, and determines the position and size of the region to be excised. Then, the incision tool 110 (see FIG. 9) such as a high-frequency knife is inserted into the channel of the endoscope 100 so that the incision tool 110 protrudes from the distal end opening. While observing the mucous membrane and the lesion with the endoscope 100, the mucous membrane around the region to be excised is marked with the incision tool 110, and then the mucous membrane is incised (step A).

Figure 4:
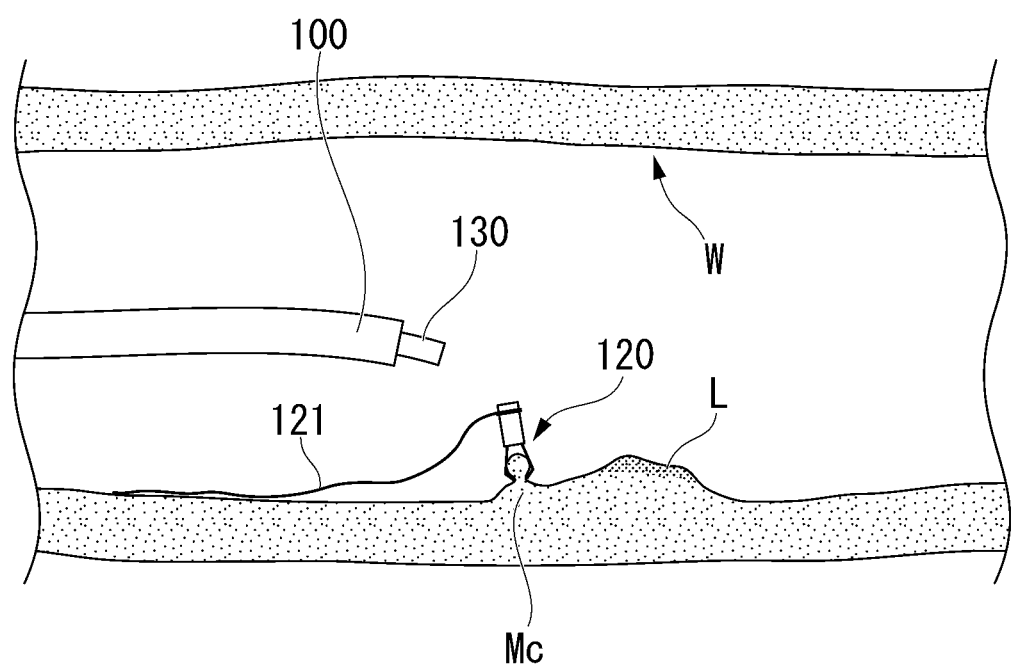
FIG. 4 is a diagram showing step B of an exemplary mucous membrane lifting method using the clip unit.

The physician then secures the thread to the mucous membrane within the region to be excised. The physician ties the first end of the thread 121 to a general clip unit 120 that does not have a thread gripping portion. Next, the incision tool 110 is replaced with the applicator 130 to which the clip unit 120 is attached, and the applicator 130 is protruded from the distal end of the endoscope 100. When the applicator 130 is operated to sandwich the mucous membrane Mc around the lesion L with the clip unit 120, the first end of the thread 121 is fixed to the mucous membrane Mc as shown in FIG. 4 (step B).

Figure 5:
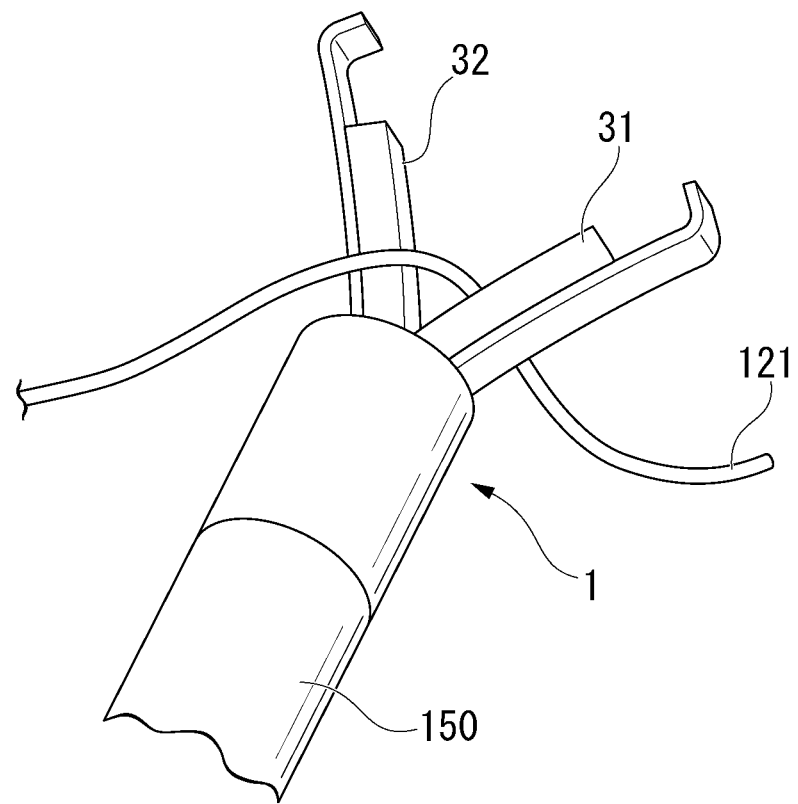
FIG. 5 is a diagram showing step C of an exemplary mucous membrane lifting method.

The physician removes the applicator 130 from the endoscope 100 and inserts the second applicator 150 with the clip unit 1 attached into the channel. The physician operates the endoscope 100 to bring the clip unit 1 closer to the thread 121, and as shown in FIG. 5, passes the intermediate portion of the thread 121 between the first member 31 and the second member 32 (step C).

In order to realize the step C, the diameter of the thread 121 needs to be smaller than the distance between the first member 31 and the second member 32 in the initial state of the clip unit 1.

Figure 6:
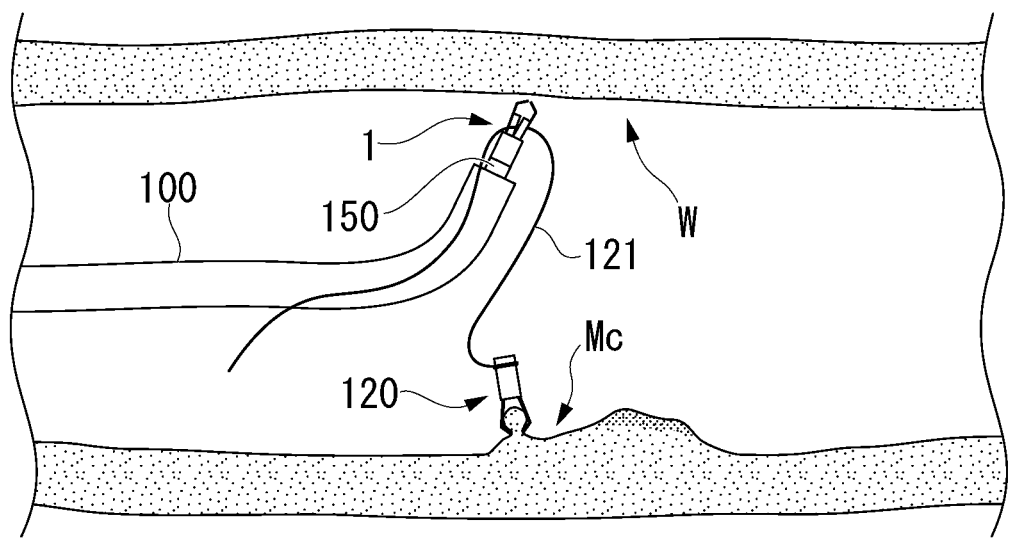
FIG. 6 is a diagram showing a step in an exemplary mucous membrane lifting method.

Next, the physician moves the distal end of the endoscope 100 toward the tube wall W of the digestive tract facing the mucous membrane Mc, as shown in FIG. 6. The clip unit 1 and the thread 121 approach the tube wall W by the movement of the distal end portion of the endoscope 100.

Subsequently, the physician fixes the clip unit 1 to the tube wall W facing the mucous membrane Mc. The physician advances the endoscope 100 to bring the claws 11a and 12a of the clip unit 1 into contact with the tube wall W.

Figure 7:
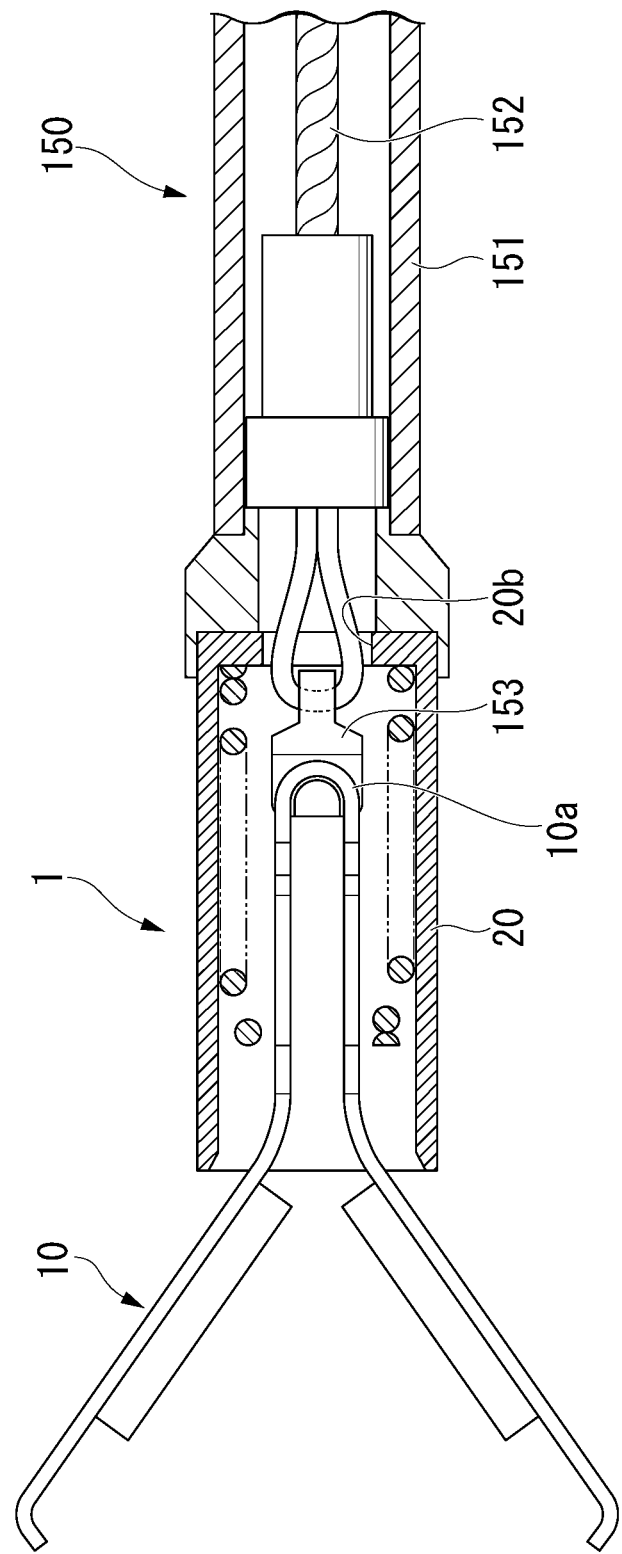
FIG. 7 is a cross-sectional view of the clip unit mounted on the applicator.

FIG. 7 shows a cross-sectional view of the clip unit 1 mounted on the second applicator 150. The second applicator 150 includes a sheath 151 and an operation wire 152 passed through the sheath 151. The manipulation wire 152 is movable within the sheath 151 along its longitudinal axis. A hook (connector) 153 is attached to the distal end of the operation wire 152. The pressing tube 20 is arranged at the distal end of the sheath 151. The hook 153 enters the holding tube 20 through the proximal end opening 20b of the holding tube 20. The clip unit 1 is attached to the applicator 150 by the hook 153 being locked to the proximal end 10a of the arm 10.

When the physician pulls the operation wire 152, the operation wire 152 and the hook 153 retract. As a result, the arm portion 10 retracts with respect to the pressing tube 20, and the first arm 11 and the second arm 12 gradually approach and close while sandwiching the tissue of the tube wall W.

Figure 8:
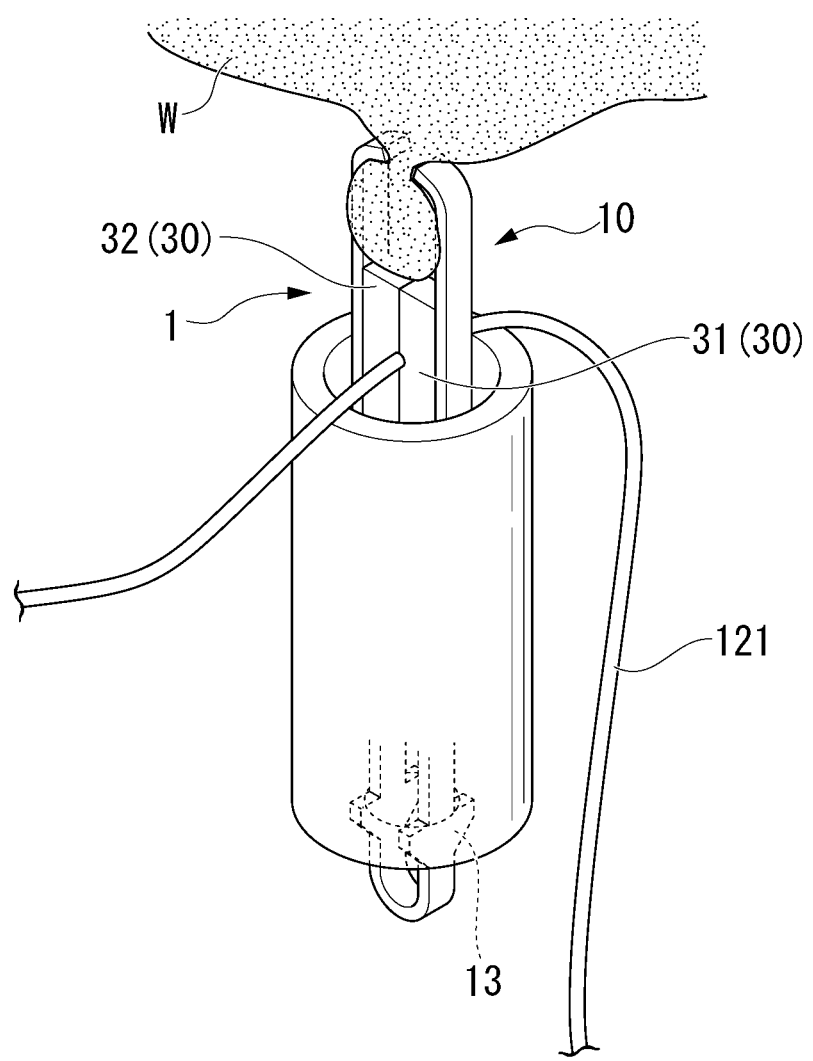
FIG. 8 is a diagram showing step D of an exemplary mucous membrane lifting method.

When the physician further pulls the operation wire 152, the operation wire 152 and the hook 153 move to the outside of the holding tube 20, and the locking portion 13 passes through the proximal end opening 20*b*. When the physician disconnects the hook 153 and the arm portion 10 in this state, as shown in FIG. 8, the state in which the arm portion 10 is closed (closed state) is maintained by the locking portion 13 that cannot pass through the proximal end opening 20*b*, and the clip unit 1 is locked to the tube wall W (step D).

In step D, the first arm 11 and the second arm 12 are closed, the distance between the first member 31 and the second member 32 of the thread gripping portion 30 is less than the diameter of the thread 121, and the first member 31 and the second member 32 are in close contact with each other with the thread 121 interposed therebetween. The first member 31 and the second member 32 are elastically deformed at least in a portion in contact with the thread 121, and generate a frictional force with the thread 121.

Figure 9:
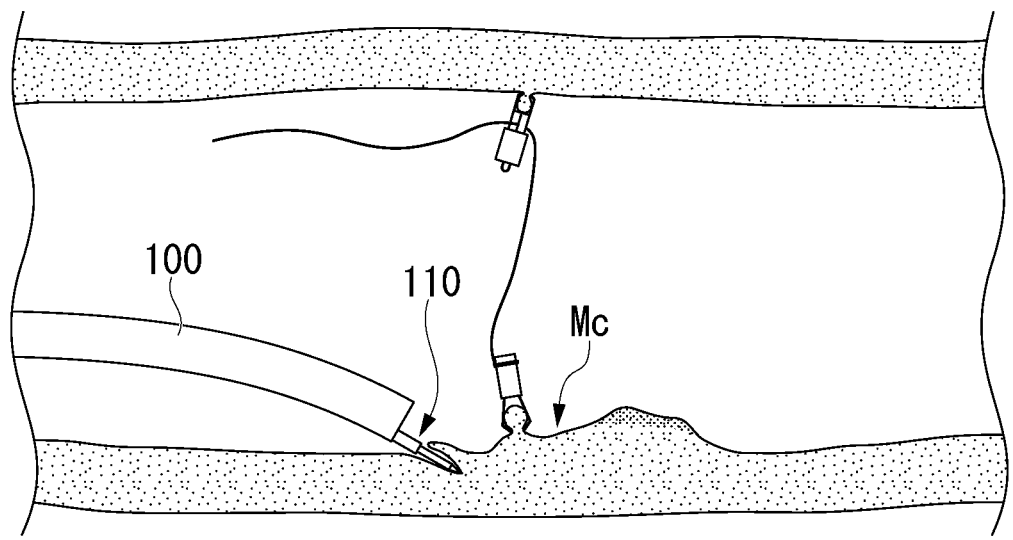
FIG. 9 is a view showing a state in which the submucous membrane layer is peeled off.

The physician removes the second applicator 150 from the channel of the endoscope 100 and inserts the incision tool 110 into the channel. As shown in FIG. 9, the physician uses the incision tool 110 to sequentially remove the submucous membrane layer under the mucous membrane Mc from the incised portion. Swelling of the site to be excised using physiological saline or the like is also performed if necessary. The incision of the mucous membrane and the peeling of the submucous membrane can be performed in the same manner as the procedure in ESD or the like.

Figure 10:
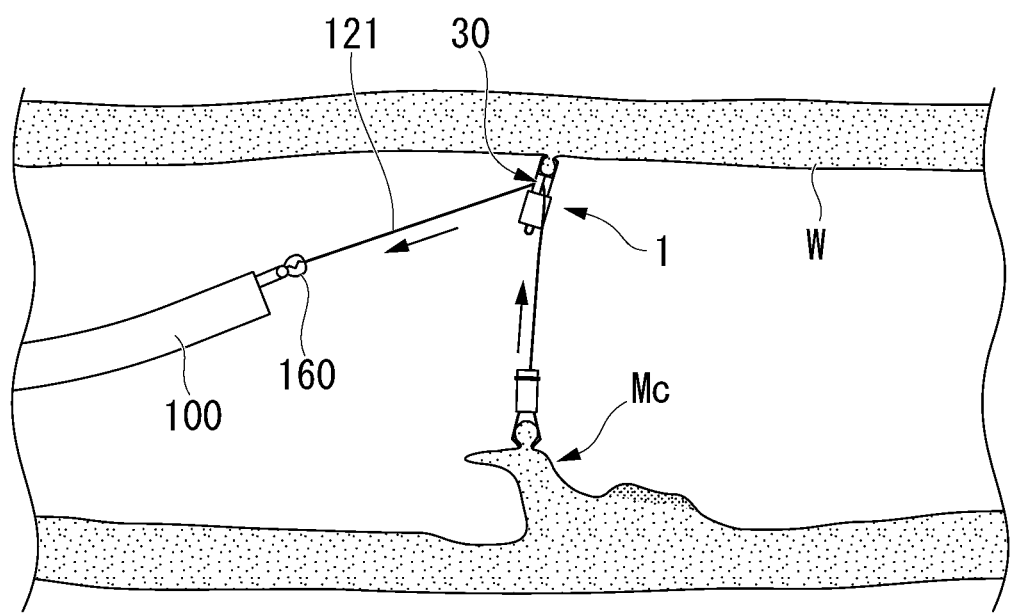
FIG. 10 is a diagram showing step E of an exemplary mucous membrane lifting method.

When the peeling of the submucous membrane layer progresses, the mucous membrane in the already peeled portion hinders the procedure, and thus the mucous membrane Mc is further lifted. The physician removes the incision tool 110 from the channel and inserts the grasping forceps 160 into the channel. As shown in FIG. 10, the physician grasps the second end portion of the thread 121 extending between the thread gripping portions 30 with the grasping forceps 160 protruding from the endoscope 100, and pulls it in a direction away from the clip unit 1. The thread 121 is supported by the frictional force generated in the thread gripping portion 30, but is not completely fixed, and therefore, when pulled with a force exceeding the frictional force, the thread 121 moves with respect to the clip unit 1. When the thread 121 moves, the clip unit 120 connected to the thread 121 approaches the tube wall W while being fixed to the mucous membrane Mc. As a result, as shown in FIG. 10, the mucous membrane Mc is lifted (step E). Gravity associated with the weight of the mucous membrane Mc acts on the thread 121, but the thread gripping portion 30 prevents the thread 121 from moving downward due to the generated frictional force, and maintains the lifted state of the mucous membrane Mc.

The pulling amount of the thread 121 in step E can be appropriately determined by the physician in consideration of the amount of peeling, the size of the excised mucous membrane Mc, the size of the traction to be applied to the lifted mucous membrane Mc, and the like. If the thread 121 is pulled too much, the thread 121 located between the clip unit 120 and the clip unit 1 may be pulled in the direction of separating from the clip unit 1, that is, in the direction opposite to the above-described pulling.

The physician manipulates the thread 121 as appropriate to further peel off the submucous membrane layer under the mucous membrane Mc while changing the lifting state of the mucous membrane and the size of the traction. After the separation of the mucous membrane Mc in the predetermined range including the lesion L is completed, the physician pulls the thread 121 located between the clip unit 120 and the clip unit 1 and pulls it out from the clip unit 1.

After that, the lesion L and the mucous membrane Mc that have been peeled and removed are collected outside the body together with the clip unit 120 and the thread 121, and a series of procedures is completed. The clip unit 1 locked to the tube wall W naturally falls off from the tube wall after a certain period of time, and is discharged to the outside of the body through the digestive tract.

According to the clip unit 1 of the present embodiment, since the thread gripping portion 30 disposed between the first arm 11 and the second arm 12 is provided, the thread locked on the mucous membrane Mc can be supported by the frictional force while being locked on the tube wall W by the first arm 11 and the second arm 12. Therefore, the direction in which the mucous membrane is pulled can be freely set according to the position where the clip unit 1 is arranged, and regardless of the direction in which the mucous membrane is pulled, only by pulling the thread 121 in the direction away from the clip unit 1, the mucous membrane can be lifted and the operability is good.

Further, in the mucous membrane lifting method using the clip unit 1, the length of the thread 121 located between the clip unit 1 attached to the tube wall W and the clip unit 120 attached to the mucous membrane can be freely changed. Therefore, unlike known mucous membrane retractors, the size of the traction applied to the mucous membrane is less likely to be affected by the physical properties of the thread 121. As a result, the size of the traction can be adjusted easily and freely.

Another exemplary embodiment of the present disclosure will be described with reference to FIGS. 11 to 14. In the following description, the same components as those already described will be designated by the same reference numerals and redundant description will be omitted.

Figure 11:
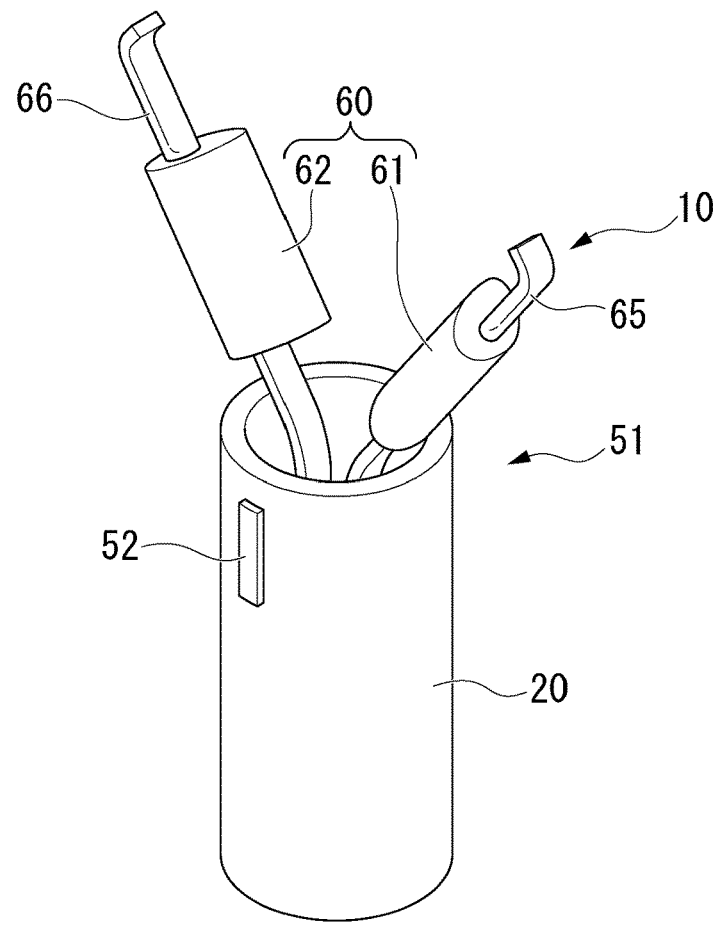
FIG. 11 is an external view of a clip unit according to an exemplary embodiment of the present disclosure.
Figure 12:
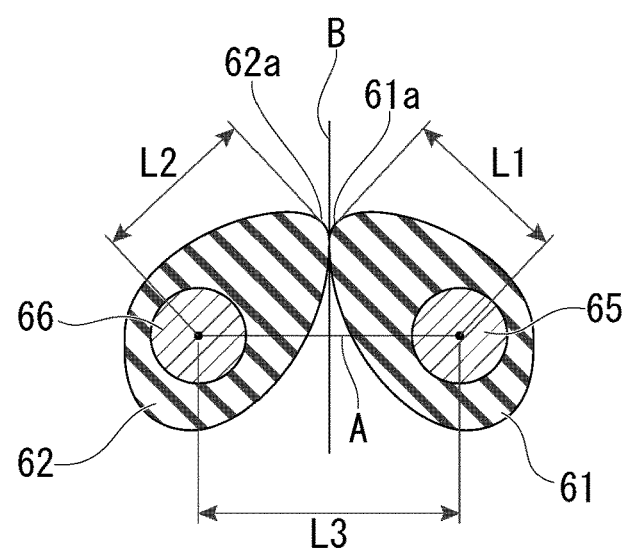
FIG. 12 is a cross-sectional view of the clip unit with the arms closed.

FIG. 11 is an external view of the clip unit 51 of this embodiment. FIG. 12 is a cross-sectional view of the clip unit 51 with the arm portion 10 closed. The clip unit 51 includes a thread gripping portion 60 including a first member 61 and a second member 62, instead of the thread gripping portion 30. Further, a first arm 65 and a second arm 66 are provided instead of the first arm 11 and the second arm 12.

The first member 61 and the second member 62 are made of the same material as that of the thread gripping portion 30 of the above embodiment. As shown in FIG. 11, the first member 61 and the second member 62 are attached so as to cover the periphery of the first arm 65 and the second arm 66.

FIG. 12 shows a cross section of the first arm 65 and the second arm 66 in the closed state of the arm portion 10. In the first arm 65 and the second arm 66, the cross sections of the parts to which the first member 61 and the second member 62 are attached are circular. Therefore, the first member 61 and the second member 62 can rotate with respect to the first arm 65 and the second arm 66, respectively.

The first member 61 and the second member 62 each have a convex shape, and the thread 121 can be sandwiched between the first member 61 and the second member 62.

In the cross section shown in FIG. 12, the convex shapes of the first member 61 and the second member 62 extend in a direction that connects the first arm 65 and the second arm 66 and is inclined with respect to both a line A (first line) that coincides with the opening/closing direction and a line B (second line) orthogonal to the line A. The sum of the length L1 from the convex apex 61*a* of the first member 61 to the first arm 65 and the length L2 from the convex apex 62*a* of the second member 62 to the second arm 66 is longer than the distance L3 between the first arm 65 and the second arm 66 when the first arm 65 and the second arm 66 are closed.

The first member 61 and the first arm 65, and the second member 62 and the second arm 66 are positioned in a state where the apex 61a and the apex 62a are close to each other as shown in FIG. 12 due to the frictional force generated therebetween.

A marker 52 is provided on the pressing tube 20. The marker 52 is formed on the outer peripheral surface on the side opposite to the side where the apex 61a and the apex 62a are located in the direction in which the line B extends, but is not limited to this embodiment. The marker 52 may have a three-dimensional shape or may be partially painted.

Figure 13:
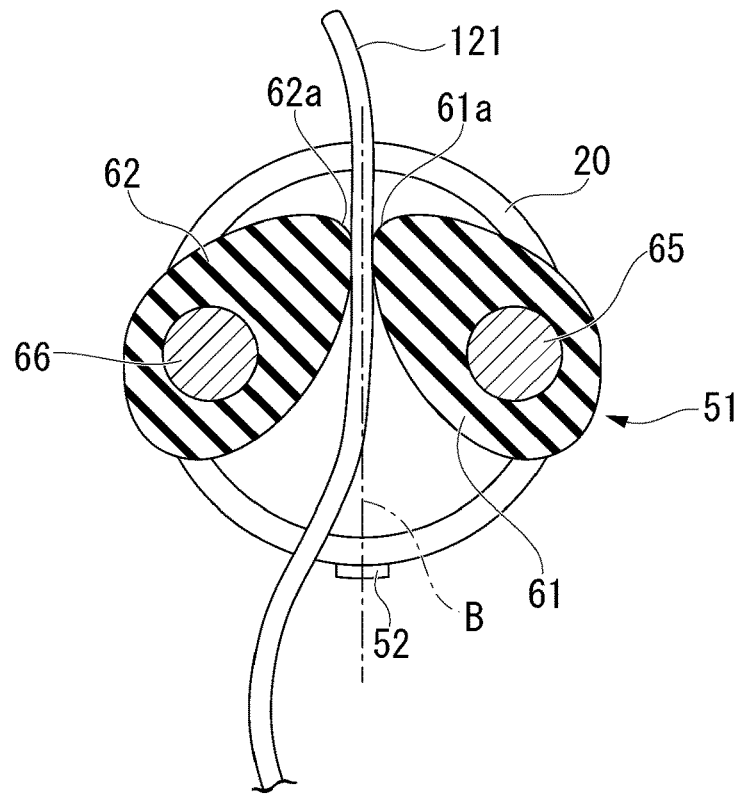
FIG. 13 is a schematic cross-sectional view showing a state in which a thread is sandwiched by a thread gripping portion of the clip unit.
Figure 14:
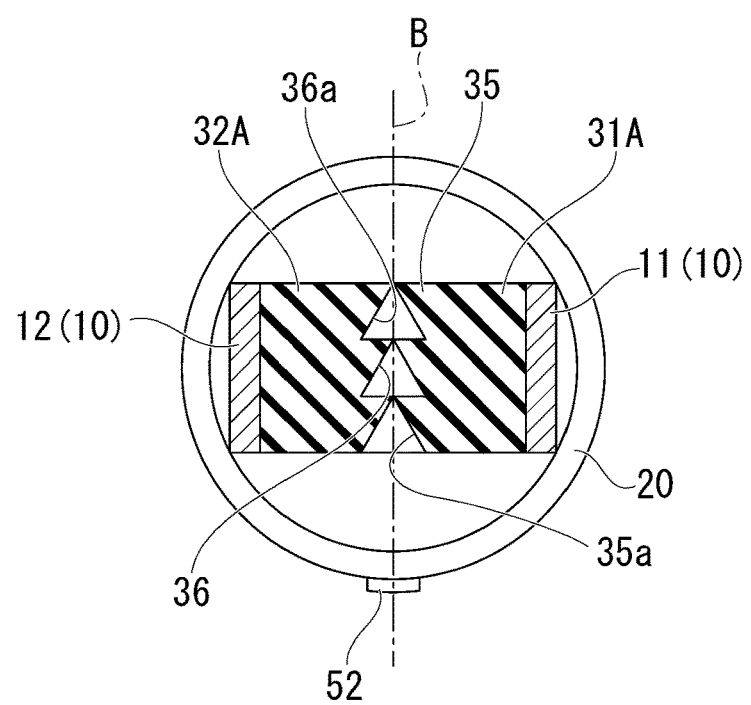
FIG. 14 is a schematic cross-sectional view showing a thread gripping portion in an exemplary embodiment of the clip unit.

The operation of the clip unit 51 of this embodiment when it is used will be described. In step C, the physician passes the thread 121 from the side where the marker 52 is provided to the thread gripping portion 60, that is, in the direction from the line A toward the apex 61a and the apex 62a. In step D, as shown in FIG. 13, the thread 121 is sandwiched between the apex 61a of the first member 61 and the apex 62a and the second member 62 at a position separated from the line A with respect to the first arm 65 and the second arm 66.

The thread 121 sandwiched between the first member 61 and the second member 62 pulls the second end side. Thereby, when moving in the direction from the line A to the apex 61a and the apex 62a, that is, in the direction from the marker 52 to the apex 61a and the apex 62a, the first member 61 and the second member 62 rotate with respect to the first arm 65 and the second arm 66, respectively. As a result, the thread 121 moves easily.

On the other hand, when the thread 121 pulls on the first end side. Thereby, even when moving in the direction from the apex 61a and the apex 62a toward the line A, that is, in the direction from the apex 61a and the apex 62a toward the marker 52, the first member 61 and the second member 62 try to rotate with respect to the first arm 65 and the second arm 66. At this time, since the sum of the lengths L1 and L2 is longer than L3, the first member 61 and the second member 62 cannot rotate or rotate while being compressed and deformed depending on the material thereof. In any case, the thread 121 receives a large resistance because the first member 61 and the second member 62 are further strongly pressed or the frictional force generated between the first member 61 and the second member 62 becomes large. As a result, the thread 121 is less likely to move than when the thread 121 moves in the direction from the line A toward the apex 61a and the apex 62a.

As described above, the thread 121 sandwiched by the thread gripping portion 60 does not easily move to the side of the mucous membrane Mc to be lifted, and maintains the lifted state in a good condition. Further, the resistance when the thread 121 is pulled in step E is small, and step E can be performed easily.

Also in the clip unit 51 of the present embodiment, as in the above embodiment, the mucous membrane can be easily lifted and the size of the traction can be easily and freely adjusted.

Furthermore, the thread gripping portion 60 is configured to receive a greater resistance in one of the moving directions of the sandwiched thread 121. Thereby, by locking the clip unit 51 to the tube wall W in a state where the thread 121 is passed through the thread gripping portion 60 in a predetermined direction, it is possible to easily adjust the lifted state while suitably withstanding the weight of the mucous membrane Mc.

In the configuration described above, only one of the first member and the second member may be rotatably attached to the arm, and the other may be attached so as not to rotate. Even such a structure has substantially the same effect.

Further, the cross-sectional shapes of the first member 61 and the second member 62 may be different from the above-described shapes as long as they have a convex shape extending in the above-described direction. For example, it may be substantially D-shaped with the opposite side being flat.

The structure of the thread gripping portion that receives different resistance depending on the moving direction of the sandwiched thread 121 is not limited to the above-described configuration. The thread gripping portion 30A of the modified example shown in FIG. 14 includes first members 31A and 32A attached to the first arm 11 and the second arm 12 in the same manner as in the above embodiment. The first members 31A and 32A have a plurality of protrusions 35 and 36 protruding toward the opposing arms, respectively. The convex portion 35 has an inclined surface 35a that is inclined in a direction away from the marker 52. The convex portion 36 has an inclined surface 36a that is inclined in a direction away from the marker 52. In the thread gripping portion 30A, the convex portion 35 and the convex portion 36 come into close contact with each other in a state where the first arm 11 and the second arm 12 are closed. Thereby, the thread sandwiched by the thread gripping portion 30A is supported by the frictional force generated between the convex portion 36 and the convex portion 36.

The thread sandwiched by the thread gripping portion 30A is supported within the range of the arm portion in the direction in which the line B extends. The frictional force generated changes depending on the direction in which the sandwiched thread moves, and as a result, the resistance received by the thread also changes depending on the direction of movement. Therefore, in the thread gripping portion of the present embodiment, it is not essential that the position where the thread is caught in the direction in which the line B extends deviates from the arm portion.

In this modified example, in step C, the thread can be satisfactorily maintained by passing the thread in the direction in which the inclined surface 35a of the convex portion 35 and the inclined surface 36a of the convex portion 36 extend toward the apex of each convex portion.

In the present embodiment, the marker 52 is not essential and may be omitted.

Furthermore, the convex shape or the convex portion may be provided only in a partial cross section of the first member and the second member.

Although the respective embodiments of the present disclosure have been described above, the technical scope of the present disclosure is not limited to the above-mentioned embodiments, and various modifications or deletion can be made to the respective components within a range not departing from the spirit of the present disclosure.

Although some modifications are illustrated below, these are not all and other modifications are possible. Two or more of these changes may be combined appropriately.

In the thread gripping portion of the present disclosure, one of the first member and the second member may be formed of a material that is not substantially elastically deformed. Even with such a configuration, it is possible to generate a frictional force with the thread by elastically deforming the other.

Figure 15:
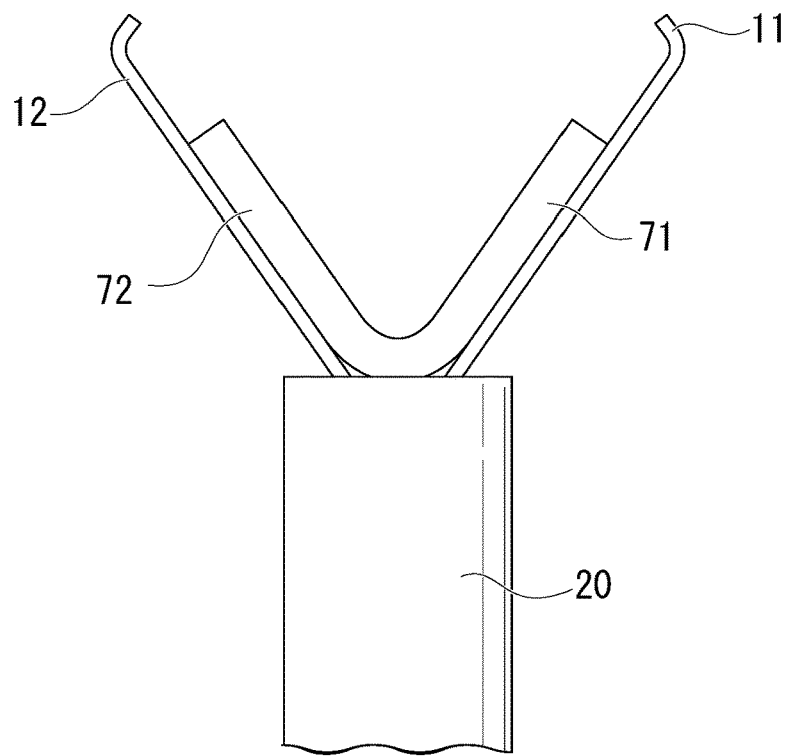
FIG. 15 is a view showing a clip unit according to an exemplary embodiment of the present disclosure.

Like the modification shown in FIG. 15, the first member 71 and the second member 72 may be connected by the proximal end part near the presser pipe 20.

The first member 81 and the second member 82 may be located outside the holding tube 20 when the arm portion 10 is closed. In this case, if the ring 83 is arranged between the first member 81, the second member 82, and the pressing tube 20 as in the modification shown in FIG. 16, it is possible to prevent the thread sandwiched between the first member 81 and the second member 82 from falling off.

Figure 16:
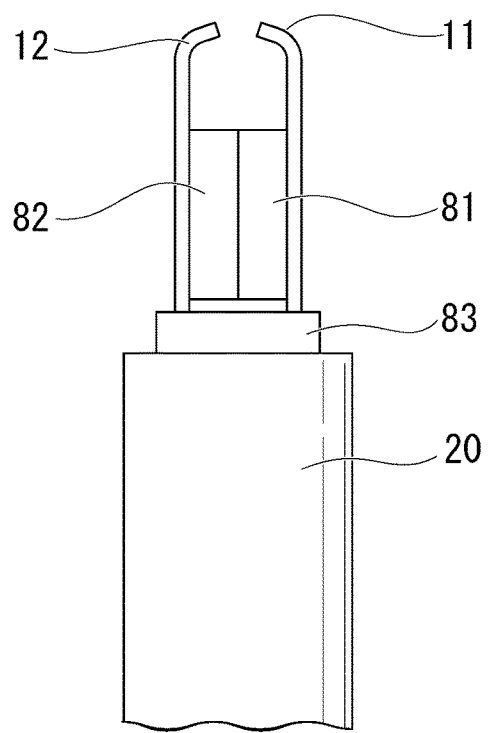
FIG. 16 is a view showing a clip unit according to an exemplary embodiment of the present disclosure.

In both of the modified examples shown in FIGS. 15 and 16, it is possible to prevent the friction force from being lost due to the thread coming off the thread gripping portion and moving between the thread gripping portion and the pressing tube.

The clip unit 120 locked to the mucous membrane Mc and the clip unit of the present disclosure locked to the tube wall W may have the same structure or different structures. In the case of the same structure, the applicator may be shared by mounting the clip unit of the present disclosure on the applicator after the clip unit 120 is locked.

The thread 121 may be locked to the mucous membrane Mc without using the clip unit. For example, the thread 121 may be locked to the mucous membrane Mc by hanging the thread on the mucous membrane Mc using a curved needle to which the thread 121 is connected.

When the endoscope has a plurality of channels, grasping forceps may be passed through a channel different from the channel through which the incision tool passes. In this case, it is not necessary to replace the incision tool with the grasping forceps in step E, and the required time can be shortened and the mucous membrane can be easily lifted.

A loop, knot, or the like may be provided at the end of the thread 121 to facilitate grasping with the grasping forceps.

In step D, the operation of the thread 121 may be performed by an instrument other than the grasping forceps. For example, when the distal end of the incision tool has a hook shape, a loop or knot may be provided on the linear member as described above, and the hook may be hung on the loop or knot to pull the linear member. The linear member may be pulled by suction, for example, by attaching to the linear member a member that can be attracted to the distal end portion of the endoscope by suction. Also in these cases, it is not necessary to replace the incision tool with the grasping forceps.

The end of the thread 121 may be pulled out of the patient's body. In this case, in step D, the mucous membrane can be lifted by directly grasping and pulling the thread 121 by the physician or the assistant, and thus the mucous membrane can be lifted without using grasping forceps, and the operation is simple.

The present disclosure can be applied to a clip unit, a mucous membrane lifting system, and a mucous membrane lifting method.

What is claimed is:

1. A clip unit for lifting a mucous membrane, comprising:
an arm portion including a first arm and a second arm extending from a proximal end portion to respective distal end portions so as to be openable and closeable with respect to each other, the first arm and the second arm each including a claw at a distal end thereof, the claw of the first arm and the claw of the second arm being configured to sandwich a biological tissue therebetween;
a holder configured to hold the first arm and the second arm in a closed state by accommodating the proximal end portion of the arm portion; and
a thread grip attached to at least one of the first arm and the second arm at a position on a proximal end side of the claw,
wherein:
the thread grip includes:
a first member rotatably attached to the first arm, and
a second member attached to the second arm,
a cross section of at least a part of the first member and the second member has a convex shape,
the convex shape extends in a direction inclined with respect to a first line extending between the first arm and the second arm, and a second line orthogonal to the first line in the cross section,
the first arm and the first member are positioned so that an apex of the convex shape of the first member is adjacent to an apex of the convex shape of the second member due to a frictional force generated between the first arm and the first member, and
a sum of a distance between the first arm and the apex of the convex shape of the first member in the cross section and a distance between the second arm and the apex of the convex shape of the second member in the cross section is longer than a distance between the first arm and the second arm in the closed state.

2. The clip unit according to claim 1, wherein a hardness of a surface of the thread grip that is configured to contact a thread is lower than a hardness of a surface of the first arm and the second arm.

3. The clip unit according to claim 1, further comprising:
a thread,
wherein:
the thread grip is configured to sandwich the thread between the first member and the second member, and
a diameter of the thread is smaller than a distance between the first member and the second member in a state where the first arm and the second arm are spread open, and is larger than a distance between the first member and the second member when the first arm and the second arm are in the closed state.

4. The clip unit according to claim 1, wherein:
in the cross section, the first member and the second member include a plurality of convex portions extending in directions approaching each other, and
in the cross section, each of the plurality of convex portions has an inclined surface that is inclined with respect to the first line extending between the first arm and the second arm, and the second line orthogonal to the first line.

5. The clip unit according to claim 1, further comprising:
an operation wire that has a distal end and a proximal end and is provided so as to be movable along a longitudinal axis; and
a connector which is located between and connects the proximal end portion of the arm portion and the operation wire;
wherein the operation wire is configured to be pulled to release the connector from the proximal end portion of the arm portion.

6. The clip unit according to claim 1, wherein a Young's modulus of the thread grip is smaller than a Young's modulus of the first arm and the second arm.

7. A mucous membrane lifting system comprising:
the clip unit according to claim 1;
a thread including a first end portion configured to be fixed to a mucous membrane, a second end portion different from the first end portion, and an intermediate portion provided between the first end portion and the second end portion and configured to be sandwiched by the thread grip of the clip unit; and grasping forceps configured to grip the second end portion of the thread to pull the thread.

\* \* \* \* \*